US010464879B2

(12) United States Patent
Moonen et al.

(10) Patent No.: US 10,464,879 B2
(45) Date of Patent: Nov. 5, 2019

(54) PROCESS FOR THE REDUCTIVE AMINATION OF HALOGEN-CONTAINING SUBSTRATES

(71) Applicant: Taminco BVBA, Ghent (BE)

(72) Inventors: Kristof Moonen, Hamme (BE); Kim Dumoleijn, Eede (NE); Kristof Weyne, Ghent (BE); Jerome Leonard Stavinoha, Jr., Longview, TX (US); Zhufang Liu, Kingsport, TN (US)

(73) Assignee: Taminco BVBA, Ghent (BE)

( * ) Notice: Subject to any disclaimer, the term of this patent is extended or adjusted under 35 U.S.C. 154(b) by 0 days.

(21) Appl. No.: 15/344,846

(22) Filed: Nov. 7, 2016

(65) Prior Publication Data

US 2017/0129847 A1 May 11, 2017

Related U.S. Application Data

(60) Provisional application No. 62/253,416, filed on Nov. 10, 2015.

(51) Int. Cl.
| | | |
|---|---|---|
| C07C 209/26 | (2006.01) | |
| A01N 37/36 | (2006.01) | |
| C07C 211/29 | (2006.01) | |
| C07C 209/78 | (2006.01) | |

(52) U.S. Cl.
CPC ............ *C07C 209/26* (2013.01); *A01N 37/36* (2013.01); *C07C 209/78* (2013.01); *C07C 211/29* (2013.01)

(58) Field of Classification Search
None
See application file for complete search history.

(56) References Cited

U.S. PATENT DOCUMENTS

| | | | |
|---|---|---|---|
| 3,499,034 | A | 3/1970 | Gonzalez |
| 3,546,297 | A | 12/1970 | Kosak |
| 3,666,813 | A | 5/1972 | Hindin et al. |
| 3,830,756 | A | 8/1974 | Sanchez et al. |
| 4,024,274 | A | 5/1977 | Druckrey et al. |
| 5,011,996 | A | 4/1991 | Kiel et al. |
| 5,512,529 | A | 4/1996 | Deller et al. |
| 5,689,021 | A | 11/1997 | Cordier et al. |
| 6,410,806 | B2 | 6/2002 | Oku et al. |
| 6,429,335 | B1 | 8/2002 | Kiel |
| 6,462,236 | B2 | 10/2002 | Liang et al. |
| 7,230,134 | B2 | 6/2007 | Borner et al. |
| 2001/0056035 | A1 | 12/2001 | Auer |
| 2007/0078282 | A1 | 4/2007 | Schramm et al. |
| 2010/0113778 | A1 | 5/2010 | Wiegand et al. |
| 2010/0274054 | A1 | 10/2010 | Staeb et al. |
| 2016/0002146 | A1* | 1/2016 | Peters .................. C07C 209/26 564/384 |
| 2016/0207874 | A1 | 7/2016 | Moonen et al. |

FOREIGN PATENT DOCUMENTS

| | | |
|---|---|---|
| CN | 102503836 A | 6/2012 |
| EP | 0 312 253 A2 | 4/1989 |
| EP | 1 195 192 A1 | 4/2002 |
| EP | 2 301 660 A1 | 3/2011 |
| EP | 2 774 911 A1 | 9/2014 |
| GB | 2 024 643 A | 1/1980 |
| WO | WO 2013/017611 A1 | 2/2013 |
| WO | WO 2014/135508 A1 | 9/2014 |
| WO | WO 2014/202436 A1 | 12/2014 |
| WO | WO 2014/202441 A1 | 12/2014 |
| WO | WO 2015/032653 A1 | 3/2015 |
| WO | WO 2016/071410 A1 | 5/2016 |

OTHER PUBLICATIONS

Wang et al.; "Single-phase bimetallic system for the selective oxidation of glycerol to glycerate"; Chem. Commun. (The Royal Society of Chemistry); 2006; pp. 1956-1958.
Enache et al.; "Solvent-Free Oxidation of Primary Alcohols to Aldehydes Using Au—Pd/TiO$_2$ Catalysts"; Science; 2006; vol. 311; pp. 362-365.
PCT International Search Report and Written Opinion of the International Searching Authority with dated Apr. 26, 2017 for International Application No. PCT/IB2016/001904.
Bagal et al.; "PS-Pd-NHC: an efficient and heterogeneous recyclable catalyst for direct reductive amination of carbonyl compounds with primary / secondary amines in aqueous medium"; Catalysis Science & Technology; 2012; 2; pp. 354-358.
Drinkel et al.; "Zwitterionic-Surfactant-Stabilized Palladium Nanoparticles as Catalysts in the Hydrogen Transfer Reductive Amination of Benzaldehydes" The Journal or Organic Chemistry; 2014; 79; pp. 2574-2579.
PCT International Search Report and Written Opinion of the International Searching Authority dated Jan. 25, 2016 for International Application No. PCT/EP2015/075734.
Co-pending U.S. Appl. No. 15/523,864, filed May 2, 2017; Moonen et al.
Cheng et al., "The effect of water on the hydrogenation of o-chloronitrobenzene in ethanol, n-heptane and compressed carbon dioxide", Applied Catalysis A: General 455, (2013), pp. 8-15.
Dan-Qian et al, "Hydrogenation of ionic liquids: An alternative methodology toward highly selective catalysis of halonitrobenzenes to corresponding haloanilines", Journal of Molecular Catalysis A: Chemical, 235, (2005), pp. 137-142.

(Continued)

*Primary Examiner* — Brian J Davis
(74) *Attorney, Agent, or Firm* — Dennis V. Carmen

(57) ABSTRACT

Disclosed is a process for performing a reductive amination of a first functional group in an organic feed substrate, which feed substrate comprises at least one further functional group containing a halogen atom, in the presence of hydrogen, a nitrogen-containing compound, and a catalyst, wherein the presence of the nitrogen-containing compound, expressed in a molar ratio relative to the first functional group in the organic feed substrate, at least during the reaction as long as the conversion of the organic feed substrate has not yet reached 80%, is maintained below a level of 1.3. Further disclosed is a composition of the invention comprising at least 98.0% wt of 2-chloro-benzyl-dimethylamine, at most 0.60% wt of the meso-o-Cl-BDMA dimer and at least 1 ppm wt of the (+/−)-o-Cl-BDMA dimer and any use therefor.

12 Claims, 2 Drawing Sheets

(56) References Cited

OTHER PUBLICATIONS

Kratky et al, "Effect of catalyst and substituents on the hydrogenation of chloronitrobenzenes", Applied Catalysis A: General, 235, (2002), pp. 225-231.

Wang et al., "A green synthesis route of ortho-chloroaniline: Solvent-free selective hydrogenation of ortho-chloronitrobenzene over Pt—Ru/$Fe_3O_4$/C catalyst", Catalysis Communications, vol. 19, (2012), pp. 110-114.

Mahata et al., "Promotional effect of Cu on the structure and chloronitrobenzene hydrogenation performance of carbon nanotube and activated carbon supported Pt catalysts", Applied Catalysis A: General 464-465, (2013), pp. 28-34.

Han et al., "Effect of transition metal (Cr, Mn, Fe, Co, Ni and Cu) on the hydrogenation properties of chloronitrobenzene over Pt/$TiO_2$ catalysts", Journal of Molecular Catalysis A: Chemical, 209, (2004), pp. 83-87.

Coq et al.:"Influence of alloying platinum for the hydrogenation of p-chloronitrobenzene over PtM/$Al_2O_3$ catalysts with M=Sn, Pb, Ge, Al, Zn", Journal of Molecular Catalysis, vol. 71, Issue 3, Feb. 1, 1992, pp. 317-333.

Tijani et al., "Hydrogenation of para-chloronitrobenzene over supported ruthenium-based catalysts", Applied Catalysis, vol. 76, issue 2, Sep. 16, 1991, pp. 255-266.

Cárdenas-Lizana et al., "Pd-promoted selective gas phase hydrogenation of p-chloronitrobenzene over alumina supported Au", Journal of Catalysis, vol. 262, (2009), pp. 235-243.

Bhattacharyya, "A high throughput synthesis of N,N-dimethyl tertiary amines", Synthetic Communications, vol. 30, No. 11, (2000), pp. 2001-2008.

PCT International Search Report and Written Opinion of the International Searching Authority dated Dec. 17, 2014 for International Application No. PCT/EP2014/068083.

PCT Second Written Opinion of the International Preliminary Examining Authority dated Sep. 8, 2015 for International Application No. PCT/EP2014/068083.

European Patent Application No. 13173233.1 filed Jun. 21, 2013; Applicant: BASF SE (Machine Translation).

European Patent Application No. 14151747.4 filed Jan. 20, 2014; Applicant: BASF SE (Machine Translation.

Co-pending U.S. Appl. No. 14/914,744, filed Feb. 26, 2016; Moonen et al.

Office Action dated Dec. 13, 2016 received in co-pending U.S. Appl. No. 14/914,744.

Notice of Allowance dated Oct. 16, 2018 received in co-pending U.S. Appl. No. 15/523,864.

Notice of Allowance dated Aug. 10, 2017 received in co-pending U.S. Appl. No. 14/914,744.

Office Action dated Feb. 7, 2018 received in co-pending U.S. Appl. No. 14/914,744.

Co-pending U.S. Appl. No. 15/678,183 filed Aug. 16, 2017; Moonen et al.

Office Action dated Apr. 6, 2018 received in co-pending U.S. Appl. No. 15/523,864.

Office Action dated May 31, 2018 received in co-pending U.S. Appl. No. 15/678,183.

Notice of Allowance dated Aug. 16, 2018 received in co-pending U.S. Appl. No. 14/914,744.

* cited by examiner

PROCESS FOR THE REDUCTIVE AMINATION OF HALOGEN-CONTAINING SUBSTRATES

CROSS REFERENCE TO RELATED APPLICATION

This application claims the benefit of Provisional Application 62/253,416 filed on Nov. 10, 2015 under 35 U.S.C. § 119(e)(1), the entire content of which is incorporated herein by reference.

FIELD OF THE INVENTION

The present invention relates to chemical reactions which involve the reductive amination of a first functional group in an organic feed substrate, in the presence of hydrogen, whereby the organic feed substrate comprises at least one further functional group containing a halogen atom and whereby the further functional group containing the halogen atom remains substantially untouched in the reaction and maintains its presence in the reaction product. In addition, the invention relates to a new product rich in 2-chloro-benzyl-dimethylamine but at the same time low in reaction by-product(s).

BACKGROUND OF THE INVENTION

The selective conversion of one functional group in a multifunctional feed substrate has been an area of continuous high interest throughout the chemical, pharmaceutical and agrochemical industry. In particular, halogen atoms are often incorporated next to other functional groups in active ingredients or in precursors of those active ingredients.

The objective of high selectivity has often been rather elusive, because most processes are prone to side reactions leading to significant amounts of by-products.

A variety of methods have been attempted in order to increase the selectivity of metal catalysed reductive aminations of one functional group in the presence of one or more halogen atoms elsewhere in the substrate molecule. A selection of such methods is discussed in WO 2015/032653 A1, which also provides literature references containing further details.

One method involves the addition of modifiers to the reaction mixture or working into alternative reaction media. In this regard, reference is made to U.S. Pat. Nos. 5,011,996, 6,429,335 B1, and US 2007/0078282 A1.

Other chemical pathways to obtain particularly valuable polyfunctional products containing halogens have also been explored. In this regard, reference is made to WO 2014/135508 A1, WO 2014/202436 A1, and WO 2015/032653 A.

The copending patent application PCT/EP2015/075734, filed on 4 Nov. 2015, discloses reductive amination reaction of 2-chloro-benzyaldehyde with DMA (dimethyl amine) to form 2-chloro-benzyl dimethyl amine (2-Cl-BDMA).

The inventors have however found that the reductive amination reactions using metal based catalysts as disclosed in the prior art may still suffer from the drawback that by-products may be formed during the reaction. The inventors have further found that particular by-products appear to have low solubility in the reaction mixture, even in significant presence of a solvent. The amount of at least one particular by-product formed can therefore rapidly exceed its solubility limit, and a precipitate may be formed. The amount of precipitate formed is small and may readily be overlooked in laboratory scale experiments, but in an industrial environment this amount may prove to be largely sufficient to cause operational problems, such as clogging filters and/or piping. In addition, the particular by-product appears act to as a poison for the heterogeneous catalyst, rapidly decreasing not only the selectivity to the desired reaction product, but also the activity to a degree that the life time of the catalyst can become unacceptably short.

There accordingly remains a need for a process to perform reductive amination reactions of halogenated substrates using a metal based catalyst in high selectivity and in which process the amount of this at least one particular type of by-product formed is reduced.

The present invention aims to obviate or at least mitigate the above described problem and/or to provide improvements generally.

SUMMARY OF THE INVENTION

According to the invention, there is provided a process, as defined in any of the accompanying process claims, a product as defined in any of the accompanying product claims, and a use of the product, as defined in any of the accompanying use claims.

The present invention relates in a first embodiment to a method for reducing the amount of a particular side-product in chemical reactions which comprise the reductive amination of a first functional group in an organic feed substrate, in the presence of hydrogen, whereby the organic feed substrates comprises at least one further functional group containing a halogen atom. More particularly, the invention relates to the metal catalysed reductive amination of only the first functional group on the substrate while keeping the further functional group containing the halogen atom substantially untouched and present in the reaction product, and at the same time reducing the amount of one or more potentially undesirable side-products or byproducts, which may be formed during the reaction.

The invention therefore provides a process for performing a reductive amination of a first functional group in an organic feed substrate, which feed substrate comprises at least one further functional group containing a halogen atom, in the presence of hydrogen, a nitrogen-containing compound, and a catalyst, wherein the presence of the nitrogen-containing compound expressed in a molar ratio, relative to the first functional group in the organic feed substrate, at least during the reaction as long as the conversion of the organic feed substrate has not yet reached 80%, is maintained below a level of 1.3.

The applicants have found that the limited presence of the nitrogen-containing compound leads to a strongly reduced formation of a potentially undesirable by-product. The applicants have found that this by-product, even in the presence of a significant amount of reaction solvent such as methanol, may even at low concentrations readily exceed its solubility limit and form a precipitate which is able to cause significant operational problems, and, in addition, can decrease the activity and the selectivity of the catalyst. The applicants have found that, by maintaining the amount of the nitrogen-containing compound within the prescribed limits, that the formation of the potentially undesirable by-product is suppressed, that the formation of this particular by-product remains sufficiently low to avoid the operational problems caused by precipitation, and that the activity and selectivity of the catalyst are maintained above commercially acceptable levels for a commercially acceptable operational period. The applicants have found that this is particularly valid for a metal containing catalyst.

In another embodiment, the invention provides for a composition comprising:
a) at least 98.0% wt (or from 98% wt to 99.999% wt) of o-chloro-benzyl-dimethylamine, o-Cl-BDMA;
b) up to 0.60% wt (or from 0.0001% wt to 0.60% wt) of (1R,2S)-1,2-bis(2-chlorophenyl)-$N^1,N^1,N^2,N^2$-tetramethylethane-1,2-diamine, herein labelled the "meso-o-Cl-BDMA dimer"; and
c) at least 1 ppm by weight, (or from 1 ppm by weight to 20,000 ppm by weight, or from 1 ppm by weight to 10,000 ppm by weight) of (1R,2R)-1,2-bis(2-chlorophenyl)-$N^1,N^1,N^2,N^2$-tetramethylethane-1,2-diamine, (1S,2S)-1,2-bis(2-chlorophenyl)-$N^1,N^1,N^2,N^2$-tetramethylethane-1,2-diamine, or mixtures thereof, including but not limited to racemic mixtures thereof, herein also collectively labelled the "(+/−)-o-Cl-BDMA dimer"; as can be measured by any method known to one of ordinary skill in the art, for example, as can be measured by gas chromatography, GC, and identifiable by gas chromatography combined with mass-spectrometry, GC-MS, in combination with nuclear magnetic resonance techniques, NMR.

The applicants have found that this composition is particularly suitable as a product for being stored, transported and/or used in further uses and applications. The applicants have found that the composition brings the advantage of a reduced risk of precipitation of the so-called meso-o-Cl-BDMA dimer. The applicants have found that the solubility limit of the meso-o-Cl-BDMA dimer at room temperature in the o-Cl-BDMA product is about 0.60% wt. The applicants have found that any precipitation of this meso-o-Cl-BDMA dimer may cause operational problems because of the possible creation of flow problems in tubes and pipes and/or through filters of the equipment holding or passing a product comprising the o-Cl-BDMA reaction product from metal catalysed reductive amination, such as in further product clean-up steps, or during storage and/or transport.

The applicants have further found that the presence of the so-called (+/−)-o-Cl-BDMA dimer, does not represent the same or a similar risk for operational problems as its (1R,2S) stereoisomer above, such as the risk for precipitation.

In this document, the term meso-o-Cl-BDMA dimer and the (+/−)-o-Cl-BDMA dimer are stereoisomers of each other, and the applicants have found that the solubility limits of the (+/−)-o-Cl-BDMA dimer and the meso-o-Cl-BDMA dimer in the reaction medium, in the reaction product, and in many other liquid environments, are significantly different. For more information about these two compounds, the applicants refer to Hatano et al., "Reductive coupling of aromatic N,N-acetals using zinc and chloromethylsilane", Tetrahedron letters 52 (2011), 3467-3469, incorporated herein by reference in its entirety.

The applicants have found that the composition according to the present invention can be particularly suitable as an intermediate for the production of more complex structures in multi-step synthesis routes. Such routes may for instance lead to agrochemical or pharmaceutical active ingredients. The applicants believe that the low presence in the composition of the meso-o-Cl-BDMA dimer reduces the risk of operational problems during transport or storage of the o-Cl-BDMA product at the location of its further commercial use, as well as in any of the further conversion steps, if present. The applicants submit that this advantage remains available throughout any conversion steps leading to further derivatives, down to the ultimate use of such derivatives by the consumer.

The inventors have found that the process according to the present invention, as well as the composition according to the present invention, reduce the need for intensive clean-up of the product from the reductive amination reaction because of the low presence of at least one by-product which—at higher concentrations—can be undesirable. The applicants have found that the presence of the (+/−)-o-Cl-BDMA dimer in the composition according to the present invention is of much less consequence for the further use of the composition, such as in many further synthesis steps and/or many uses of the products thereof. The applicants have therefore found that significant levels of the (+/−)-o-Cl-BDMA dimer may be tolerated in the composition according to the present invention and/or in the product of the process according to the present invention.

The composition can also be particularly useful if such further conversion steps comprise metallation reactions such as lithiation or Grignard reactions, such as described in US 2010/0113778 A1, or coupling reactions such as the reactions known as the Heck, the Sonogashira, the Suzuki or the Stille coupling.

In yet another embodiment, the invention provides for the use of the composition according to the present invention for the production of a fungicide, for instance, including but not limited to the subjection of the 2-Cl-BDMA in the composition to a Grignard reaction, comprising for example in a first step the preparation of a Grignard reagent in which a magnesium atom is introduced in between the benzene ring and the chlorine atom, followed by a second step wherein the Grignard reagent is esterified with an oxalic acid dialkyl ester.

The use according to the present invention may in one embodiment further comprise the production of a methoximinophenylglyoxylic ester, in another embodiment further including the production of the fungicide composition including the methoximinophenylglyoxylic ester, and in another embodiment further including the step of using the fungicide composition comprising the ester for treating a substrate.

The present invention has at least one of the following advantages: reduced operational problems and/or reduced complexity of the operations throughout the production of the subsequent further intermediates as well as the final chemical derivative, as well as in the formulation of the fungicide and during its use for treating a substrate with the fungicide formulation.

DETAILED DESCRIPTION

Figure 1:
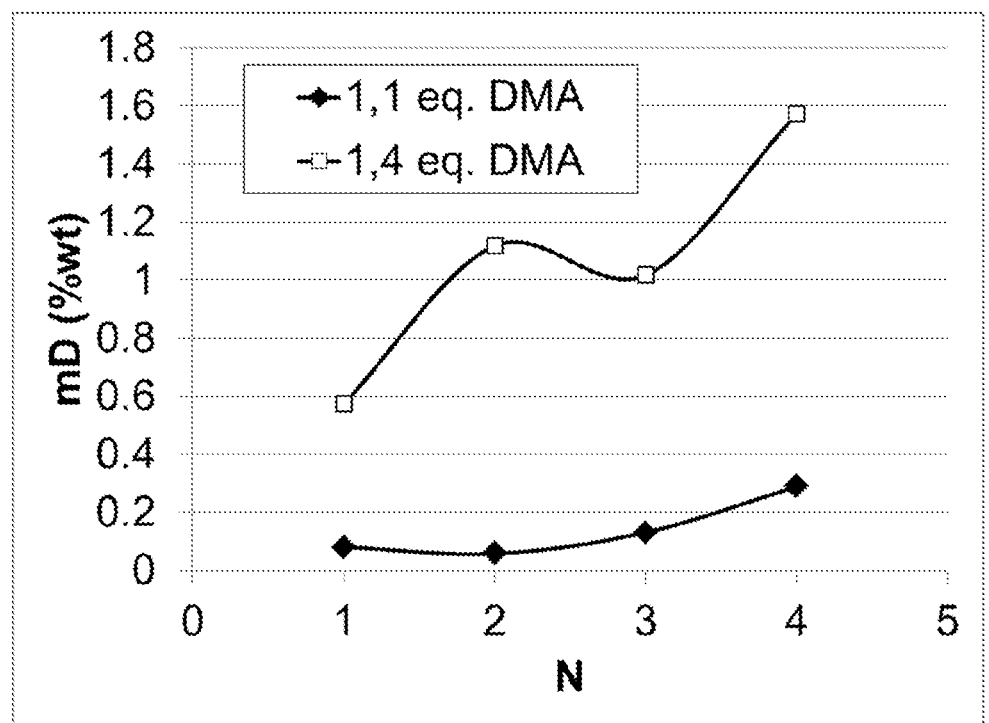
FIG. 1 contains a graph of mD (wt %) vs N, showing the evolution of the amount of the meso-o-Cl-BDMA dimer which was found in the reaction mixture from the experiments described in Example 4 below, expressed in wt % relative to the amount of 2-Cl-BDMA product retrieved in the same sample, in the reaction products from the consecutive batch runs.

The present invention will be described in the following with respect to particular embodiments and with reference to certain drawings but the invention is not limited thereto but only by the claims. Any drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention.

Furthermore, the terms first, second, third and the like in the description and in the claims, are used for distinguishing between similar elements and not necessarily for describing a sequential or chronological order. The terms are interchangeable under appropriate circumstances and the embodiments of the invention can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the invention described herein can operate in other orientations than described or illustrated herein.

The terms "ortho", "meta" and "para", abbreviated by o-, m-, p-respectively, are used to indicate the relative position of two substituents on an aromatic cycle, as defined by the International Union of Pure and Applied Chemistry (IUPAC). Taking the standard priority rules for functional groups and substituents into account, their positioning may also be referred to by numbers in chemical nomenclature. In this respect, the indication 2-, 3-, and 4- correspond to o-, m-, and p- respectively.

Reductive amination is the reaction well known in chemistry for the synthesis of primary or secondary amines starting from a suitable ketone or aldehyde. The term "amination" relates to the reaction part in which an amine functionality is incorporated into the substrate. The term "reductive" relates to the observation, when comparing the feed substrate and the product of a reductive amination reaction, that a reduction has necessarily also taken place. In chemistry, a reduction reaction refers in general to the gain of electrons of an atom or a molecule. In organic chemistry, reductions are usually related with the disappearance of unsaturated functionality, such as double bonds, from the substrate molecules. The net result of a reductive amination of a ketone or aldehyde is the conversion of a C=O double bond into a C—N single bond.

In an embodiment of the process according to the present invention, the molar ratio of the nitrogen-containing compound, relative to the first functional group in the organic feed substrate, is maintained at least during the prescribed period of the reaction at a level of at least 0.10, in other embodiments at least 0.20, at least 0.25, at least 0.30, at least 0.50, at least 0.75, at least 0.80, at least 0.90, at least 0.95, at least 0.98, at least 1.00, at least 1.01, least 1.02, at least 1.03, at least 1.04, at least 1.05, at least 1.06, at least 1.07, least 1.08, at least 1.09, at least 1.10, at least 1.12, at least 1.14, or at least 1.15. In certain embodiments, the molar ratio of the nitrogen-containing compound, relative to the first functional group in the organic feed substrate, can be maintained at least during the prescribed period of the reaction at a level of 0.1 to 1.3 or 0.2 to 1.3 or 0.3 to 1.3 or 0.4 to 1.3 or 0.5 to 1.3 or 0.6 to 1.3 or 0.7 to 1.3 or 0.8 to 1.3 or 0.9 to 1.3 or 1.0 to 1.3 or 0.1 to 1.2 or 0.2 to 1.2 or 0.3 to 1.2 or 0.4 to 1.2 or 0.5 to 1.2 or 0.6 to 1.2 or 0.7 to 1.2 or 0.8 to 1.2 or 0.9 to 1.2 or 1.0 to 1.2 or 0.1 to 1.1 or 0.2 to 1.1 or 0.3 to 1.1 or 0.4 to 1.1 or 0.5 to 1.1 or 0.6 to 1.1 or 0.7 to 1.1 or 0.8 to 1.1 or 0.9 to 1.1 or 1.0 to 1.1. The applicants have found that a higher presence of the nitrogen-containing compound in the reaction is strongly desired, as it has a beneficial effect on the formation of the intermediary imine and therefore on the overall reaction rate. The applicants have found that a relatively small stoichiometric excess of the nitrogen-containing compound is preferable, because it reduces the risk of local starvation of the nitrogen containing compound and hence a risk of breakthrough of unreacted organic feed substrate or the corresponding hydrogenated product into the reaction product. In several instances, the organic feed substrate or the corresponding hydrogenated product may be difficult to remove from the desired reaction product on an industrial scale by means of economically acceptable separation processes. Any feed substrate remaining in the product may also be of nuisance in any downstream conversion process to produce a further derivative. In addition, the unreacted feed substrate may not be recoverable in a condition wherein it may be recycled to the reductive amination process, and may hence represent a loss of raw material in addition to a nuisance for its disposal.

In an embodiment of the process according to the present invention, the molar ratio of the nitrogen-containing compound, relative to the first functional group in the organic feed substrate, is maintained in certain embodiments at a level of less than 1.25, at most 1.24, at most 1.23, at most 1.22, at most 1.21, at most 1.20, at most 1.18, at most 1.16, at most 1.14, at most 1.12, at most 1.10, at most 1.08, at most 1.05, at most 1.03, at most 1.01, at most 1.00, at most 0.90, at most 0.80, or at most 0.75. The applicants have found that the lower the excess of the nitrogen containing compound, the lower the tendency for producing the potentially undesirable by-product. The applicants believe that a lower presence of the nitrogen containing compound reduces the presence of the imine or equivalent intermediate in the reaction mixture, and that this lower presence of the particular intermediate is the cause of a lower formation of the potentially undesirable dimer, in the production of o-Cl-BDMA this being the meso-o-Cl-BDMA dimer. Without wishing to be bound by this theory, the applicants believe that the formation of the intermediary imine or other compound by the amination of the organic feed substrate is in many instances forming an equilibrium. The applicants further believe that the rate limiting step in the overall target mechanism is the subsequent hydrogenation of the intermediate (imine or other) to the final product. The molar ratio of the nitrogen-containing compound relative to the organic feed substrate is in one embodiment about to 1, in another embodiment about to 1.0, and in another embodiment about to 1.00.

In an embodiment of the process according to the present invention, the nitrogen-containing compound is at least during the prescribed period of the reaction added gradually, i.e. the addition may continue while the reductive amination reaction may already be ongoing. The applicants have found that this mode of operation is a very convenient way to keep the amount of the nitrogen containing compound low and preferably within the prescribed boundaries. Once the reaction has reached a significant level of conversion of the organic feed substrate, such as the conversion level specified in claim 1, a higher amount of nitrogen-containing compound may optionally be added, possibly such amounts that the prescribed limits may be surpassed. The applicants have found that this may be performed without jeopardizing the achievement of the desired technical effect of a low production of the potentially undesirable by-product. An advantage of the gradual addition of the nitrogen-containing compound, and building a stoichiometric excess when the conversion of the organic feed substrate has already reached significant levels, for instance as specified in claim 1, is that the benefit of a low production of the potentially undesirable by-product may be suppressed significantly, while within an economically acceptable reaction time an economically interesting and even high conversion of the organic feed substrate within the reaction medium may be obtained. Although not limited by this particular theory, formation of the potentially undesirable dimer side-product is believed to occur primarily, if not exclusively, from the substrate and intermediate substrate-amine adducts, but not anymore from the end product. The direct coupling of 2 o-Cl-BDMA molecules into a dimer could so far not be observed.

In an embodiment of the process according to the present invention, the reductive amination reaction is performed in certain embodiments until at least 50% of the organic feed substrate present in the reaction medium is converted, at least 80%, at least 90%, at least 95%, at least 98%, at least 99.0%, at least 99.5%, or until at least 99.8% of the feed substrate present in the reaction medium is converted. A higher conversion of the organic feed substrate brings the advantage of a more effective process, because more desired product is produced from the same amount of starting material. The higher conversion also brings the advantage of a more efficient process, because less raw material is left over in the reaction product, and, if a recycle of this unreacted raw material is possible from the reaction product to the reaction feed, the process requires a lower amount of recycle material. Another advantage of a higher conversion of the organic feed substrate is that less unreacted feed substrate is left in the reaction product. Because typically the unreacted feed substrate is at least undesirable in the reaction product in view of its further application and/or end-use, and often a nuisance, large amounts of unreacted feed substrate in the reaction product typically need to be removed from the desired product. Such removal operation may be difficult and complex, and may become economically unacceptable. Performing the process according to the present invention at a relatively high conversion of the organic feed substrate in the reaction medium therefore reduces or even avoids at least some of the problems brought forward in this context.

In certain embodiments of the process according to the present invention, the molar ratio of the nitrogen-containing compound relative to the first functional group in the organic feed substrate is maintained within the prescribed limits during the reaction until the conversion of the organic feed substrate present in the reaction medium has reached 80%, at least 85%, at least 90%, at least 95%, at least 98%, at least 98.5%, at least 99.0%, at least 99.4%, at least 99.6%, or at least 99.8%. The applicants have found that the formation of the potentially undesirable by-product may be further suppressed by extending the period during which the molar ratio is maintained within the limits specified in the claims. While reaction rate considerations may intuitively induce a desire for adding more of the nitrogen-containing compound, in particular when the conversion of the organic feed substrate has reached significant levels, the applicants have found that the dimer formation may be further suppressed by adhering to the molar ratio limits as specified in the claims for a longer portion of the total time during which the chemical reaction is practised as part of the process according to the present invention. The applicants believe that this is because the rate limiting step is not the amination of the substrate but the subsequent hydrogenation step.

In an embodiment of the present invention, the reductive amination reaction is performed in a reaction medium comprising a solvent. In the context of the present invention a solvent is a compound which does not take part in the chemical reaction and which is capable of reducing the concentration in the reaction medium of any of the other compounds, such as reagents, catalysts and reaction products. The applicants have found that the presence of a solvent in the reaction medium, and the higher this presence the better, may further suppress the formation of the potentially undesirable reaction by-product. Without wishing to be bound to this theory, the applicants believe that the formation of the potentially undesirable by-product involves a dimerization reaction, i.e. the reaction of one molecule of a particular compound with a second molecule of that same particular compound. The applicants believe that this is a suitable explanation for the finding that the presence of a solvent, which reduces the concentration of all active compounds in the reaction medium, has a stronger suppressing effect on the dimerization step for forming the potentially undesirable by-product as compared to any effect it may have on the competing reaction leading to the desired end-product.

In an embodiment of the process according to the present invention, the reductive amination reaction is performed in one single process step, meaning that the amination and the subsequent hydrogenation reaction are performed simultaneously and in the same reaction equipment. The applicants have found that this feature brings the advantage that the presence of the intermediate imine compound is kept low throughout the production scheme, because the intermediate, as soon as it is formed by the amination reaction, may readily further react to a compound which is not as prone to a dimerization reaction as compared to the imine intermediate itself.

In certain embodiments of the process according to the present invention, the nitrogen containing compound is selected from the list of ammonia, primary amines, secondary amines, and combinations thereof, selected from alkyl and aryl amines, dialkyl amines; or amines having the formula R1-NH—R2, wherein R1 and R2 are independently selected from a $C_1$ to $C_{10}$ alkyl group and an aryl group, optionally substituted with an alkyl group; or in certain embodiments with the R1 and/or R2 being $C_1$ to $C_4$ alkyl; or the nitrogen containing compound being dimethyl amine.

In an embodiment, the process according to the present invention is performed in continuous mode. The applicants have found that the catalyst itself, as well as its performance, may be arranged to be fairly stable over time, such that the process is highly suitable for a continuous operating mode. This brings significant advantages in terms of production rate, volumetric efficiency of the process equipment, control equipment, steadiness of performance, operator attention and intervention frequency, automation capabilities, many of which represent significant advantages to the process owner. A further advantage is brought because a continuously operated process allows to keep the concentration of the imine intermediate, which is believed to be the precursor of the potentially undesirable by-product, low if not at a minimum.

The applicants have found that the process according to the present invention may also be performed in batch mode. The applicants have found that the catalyst, upon separation from the reaction medium after a first performance of the process, may readily be reused in a second performance of the process, preferably without any intermediate treatment. The applicants have found that in certain embodiments at least 5, at least 10, and at least 15 reuse cycles may be performed with the same catalyst in the process according to the present invention. The applicants have found that some metal may leach from the catalyst during the early performances of a fresh catalyst in the process according to the present invention, but that such metal leaching is at a level which is substantially insignificant in terms of amount of metal lost from the catalyst, and also does not cause any substantial loss of performance of the catalyst.

In an embodiment of the process according to the present invention, the reductive amination reaction is performed in at least one continuous stirred tank reactor, commonly abbreviated as CSTR, for example a loop reactor. This brings the advantage that the reductive amination reaction is taking place in a reaction medium approaching the reactor product composition, i.e. with a low or reduced concentration of the reaction feed substrate but also a low concentration of the intermediate compound, which is believed to be the precursor of the potentially undesirable by-product. The applicants have found that this feature is a strong further contributor to the desired suppression of the formation of the potentially undesirable by-product. The applicants have found that this type of reactor allows to further reduce the risk for local occurrence of high concentrations of the intermediate, and hence contributes in suppressing the dimerization of the intermediate, thereby reducing the formation of the potentially undesirable by-product.

In an embodiment according to the present invention, the reductive amination reaction is performed in at least one continuous plug flow reactor. The applicants have found that a plug flow reactor is particularly suitable for performing the reductive amination reactor therein, in particular for obtaining high reaction rates when the reaction reaches completion, such as for pushing the reaction when the conversion of the organic feed substrate has already reached at least 50%.

The applicants have found that the reaction may be performed in a combination of reactors of different types, for example a series arrangement with a CSTR early in the reactor chain and a plug flow reactor later in the reactor chain or series. This brings the advantage that zones of high concentration of the organic feed substrate are avoided, while higher reaction rates may be obtained for pushing the reaction to completion. The applicants submit that a series of reactors brings the extra advantage that the feed of the nitrogen-containing compound to the reaction may readily be distributed over the different reactors, such that also the concentration of this compound in the reaction mixture may be kept limited. The applicants have found that all these features in the reaction setup may contribute to and collaborate in a further suppression of the formation of the potentially undesirable by-product.

In an embodiment of the process according to the present invention, the reductive amination is performed in two steps, in the first step reacting the aldehyde with the nitrogen containing compound, and in the subsequent step introducing hydrogen and the catalyst; in one embodiment the two steps are performed in the same reaction vessel. The general mechanism of reductive aminations is believed to start with the nucleophilic addition of ammonia or a primary or secondary amine species to the carbonyl group of the ketone or aldehyde. Such addition may occur with or without the aid of a catalyst. The resulting adduct, sometimes referred to as "hemiaminal", may react further by the elimination of water to the corresponding imine, enamine or other adduct.

The second step in the mechanism of the reductive amination involves a reduction step. All three of an imine, a hemiaminal or an enamine may be the substrate before and on which the reduction is taking place. For this step, a reducing agent is required, which itself will be oxidized after the reaction has been effectuated. Such as for other hydrogenation reactions, stoichiometric reagents are sometimes used for this purpose, such as for instance formic acid or hydrides such as borohydrides or aluminium hydrides. In one embodiment, the use of hydrogen gas is particularly favourable.

According to the present invention, the reductive amination is performed in certain embodiments at a $H2$ partial pressure in the range of 0.01-250 bar gauge, at least 0.1, at least 1, at least 5.0 bar gauge, at least 10.0 bar gauge, at least 20 bar gauge, at least 30 bar gauge, at least 40 bar gauge, at least 50 bar gauge, at least 60 barg, at least 70 barg, at least 75 barg, at least 80 barg, at least 85 barg, at least 90 barg, or at least 95 bar gauge, and optionally at most 200 bar gauge, at most 150 bar gauge, at most 100 bar gauge, at most 80, at most 70, and at most 60 bar gauge. The applicants have found that a higher presence of hydrogen may contribute significantly in suppressing the formation of the potentially undesirable by-product. The applicants believe that this is because a higher presence of hydrogen increases the reaction rate of the desired hydrogenation of the intermediate compound towards the desired reaction product, in competition with the undesired dimerization reaction of the intermediate into the potentially undesirable by-product.

In certain embodiments of the process according to the present invention, the reductive amination is performed at a temperature in the range of 0-300° C., at least 10° C., at least 20° C., at least 30° C., at least 40° C., at least 60° C., at least 80° C., or at least 90° C., and optionally at most 250° C., at most 200° C., at most 180° C., at most 150° C., at most 130° C., at most 120° C., at most 110° C., or at most 100° C. The applicants have found that a lower reaction temperature contributes also in a significant way to a reduction in the formation of the potentially undesirable by-product.

In an embodiment of the process according to the present invention, the halogen atom is selected from the list consisting of chlorine, bromine, iodine, fluorine and combinations thereof. The applicants have observed that organic feed substrates containing any one of these halogen atoms in their further functional groups are particularly prone to dehalogenation as compared to other halogens such as fluorine, in particular during the reductive amination reactions in accordance to the present invention. The applicants believe that the present invention is therefore particularly relevant and suitable to perform reductive amination reactions on organic feed substrates containing these particular halogen atoms.

The halogen atom (X) is an element selected from group 17 in the IUPAC periodic table dated 22 Jun. 2007. In an embodiment of the process according to the present invention, the further functional group is selected from the list consisting of a chloride, a bromide iodide and a fluoride. In one embodiment, the further functional group is selected form of a chloride, a bromide and an iodide. The halogen is typically attached to the substrate by means of a covalent bond with a carbon atom (C—X bond). The carbon atom to which the halogen is attached may be either sp, $sp^2$ or $sp^3$ hybridized.

In an embodiment of the process according to the present invention, the first functional group is selected from the list consisting of an aldehyde, a ketone, an imine and an oxime, and combinations thereof. Reducible functional groups which may suitably be converted according to the process of the present invention are ketones, aldehydes, imine and oxime groups. Such functional groups may be present in the substrate already when this is entered into the reactor, but may also be generated in situ during the course of a chemical reaction.

In an embodiment of the process according to the present invention, the first functional group in the feed substrate is first converted in situ by reaction with an additional reagent to form a reducible functional group. In particular, ketones and aldehydes may be converted to various intermediates, under the conditions of a reductive amination reaction, and which intermediates are subsequently hydrogenated with hydrogen to the final product of the reaction.

The applicants have found that the process according to the present invention may particularly be suitable for the reductive amination of a halo-benzaldehyde in the presence of a nitrogen containing compound, in one embodiment with the nitrogen compound being selected from ammonia, a primary amine and a secondary amine, and mixtures thereof, and in another embodiment for the production of ortho-chloro benzyl dimethyl amine, o-Cl-BDMA, by the reductive amination of ortho-chloro-benzaldehyde in the presence of dimethyl amine, DMA. The applicants have found that the process according to the present invention may produce the desired o-Cl-BDMA, also known as ortho-Cl-BDMA or 2-Cl-BDMA, in very high yield and in particularly high purity, with very little by-products, and with reduced operational problems, in addition to an extended useable life time of the heterogeneous catalyst used in the reductive amination part of the production process.

For a reductive amination, chloro benzaldehydes (ortho, meta or para) are particular interesting substrates, as they may lead to the corresponding chloro benzylamines. Both the chloro and the amine functionality in these reaction products make the products of interest as further chemical building blocks, because the functionalities represent suitable points for further functionalization in subsequent synthesis steps. The chlorine atom offers opportunities for metallation reactions, such as lithiation or Grignard reactions, while the amine group offers possibilities for a further reductive amination or in case of a tertiary amine for quaternisation and conversion into other suitable leaving groups.

In an embodiment of the process according to the present invention, the catalyst comprises at least one metal. In the context of the present invention a metal is defined as a chemical element from the IUPAC periodic table of the elements, the version of 22 Jun. 2007 and wherein the element groups are numbered from 1 to and including 18, the metal being selected from the groups of transition metals and main group metals, and which metal elements are located in that periodic table of the elements to the left of the semi-metals or metalloids, the latter being located on a diagonal line from boron (B) to astatium (At).

In an embodiment of the process according to the present invention, the catalyst is a homogeneous catalyst. A homogeneous catalyst in the context of the present invention contains the metal in a form which is soluble and dissolved in the reaction medium. Suitable homogeneous catalysts are organometallic catalysts, i.e. where the metal is in an atomic form and bound to one or more donor ligands. Such organometallic compounds are often referred to as a complex. The more suitable catalysts are formed by one complex homogeneous catalyst which comprises at least one element selected from group 8, 9 and 10 of the IUPAC periodic table of elements dated 22 Jun. 2007. In one embodiment the metal is selected from iron, cobalt, nickel, ruthenium, rhodium, palladium, osmium, iridium and platinum. The complex catalyst comprises in one embodiment at least one donor ligand. Suitable donor ligands may for instance be phosphines and/or phosphites.

In certain embodiments of the process according to the present invention wherein the catalyst is homogeneous, the homogeneous catalyst is present in an amount of at least 0.01% wt relative to the total reaction mixture, at least 0.02% wt, at least 0.05% wt, at least 0.10% wt, at least 0.15 or even 0.2% wt, at least 0.3% wt, at least 0.4% wt, or at least 0.5% wt, and optionally at most 10% wt relative to the total reaction mixture. The applicants have found that a higher presence of the catalyst also contributes in a significant way to the suppression of the formation of the potentially undesirable by-product. The applicants believe that this is because a higher presence of catalyst for catalysing the hydrogenation of the intermediate compound into the desired end-product of the reductive amination reaction, increases the reaction rate thereof in comparison of the undesired dimerization of the intermediate into the potentially undesirable by-product.

In an embodiment of the process according to the present invention, the catalyst is a heterogeneous catalyst. Suitable heterogeneous catalysts are hydrogenation catalysts known in the art. Heterogeneous hydrogenation catalysts are catalytically active elements or compounds which may be available in the form of particles, or they may have been put onto a carrier or support, for instance (usually activated) carbon, silica or silicon dioxide, calcium carbonate, silicon oxide, clay, zeolite, porous polymer, zirconium dioxide or an aluminium oxide, such as AlO2 or Al2O3. and combinations thereof.

In an embodiment of the invention, hydrogenation catalysts comprise at least one active metal, either in elementary form or in the form of a compound, for instance oxides. Examples of catalysts containing metals in their elementary form are sponge nickel or sponge cobalt catalysts, for example, Raney-nickel and Raney-cobalt. Often the catalyst comprises a mixture of active metals. The metals may possibly be present in ionic form or as covalently bound. When oxides of the active metals are used, the process usually comprises a reduction of the oxide to the elementary metal, typically at higher temperatures, usually in the presence of hydrogen. This reduction step may occur at the start of the chemical conversion according to the present invention, or may be performed in a separate step prior to the conversion.

In one embodiment, the hydrogenation catalyst(s) useful in the invention are selected from at least one of the metals of groups 4, 5, 6, 7, 8, 9, 10, 11 and 12 in the IUPAC periodic table of elements dated 22 Jun. 2007.

In one embodiment, the hydrogenation catalyst(s) useful in the invention are selected from at least one of the following metals: nickel, palladium, platinum, cobalt, rhodium, iridium, copper, manganese, tin or ruthenium.

In yet another embodiment, the hydrogenation catalysts useful in the invention contain at least one metal of the cobalt, nickel or copper group of the periodic system, in particular at least one metal selected from cobalt, rhodium, iridium, nickel, palladium, platinum and copper. In certain embodiments the total concentration of the metals from the cobalt, nickel and copper group in the catalyst is at least 5% wt, at least 20% wt, or at least 50% wt relative to the total sum of all active metals in the catalyst, whereby with compounds such as oxides only the metal part of the compound is taken into account. In special embodiments, mixtures of the listed metals can be used. Further active metals which can be used in combination with the metals of the cobalt, nickel or copper group, are for instance manganese, tin, ruthenium, but also the alkali metals and the earth alkali metals.

In certain embodiments, the hydrogenation catalyst comprises cobalt, nickel, copper or mixtures of these three metals in a total concentration of at least 5% wt, at least 20% wt or at least 50% wt, based on the total of all the active metals in the catalyst.

In certain embodiments of the process according to the present invention wherein the catalyst is heterogeneous, the heterogeneous catalyst is present in an amount of at least 0.1% wt relative to the total reaction mixture, at least 0.2% wt, at least 0.5% wt, at least 1.0% wt, at least 1.5% wt, or 2% wt, at least 3% wt, at least 4% wt, at least 5% wt, at least 7% wt, at least 8% wt, or at least 10% wt. The applicants have found that a higher presence of the catalyst also contributes in a significant way to the suppression of the formation of the potentially undesirable by-product. The applicants believe that this is because a higher presence of catalyst for catalysing the hydrogenation of the intermediate compound into the desired end-product of the reductive amination reaction, increases the reaction rate thereof in comparison of the undesired dimerization of the intermediate into the potentially undesirable by-product. In an embodiment of the present invention, the heterogeneous catalyst is present as a fixed bed in a reactor, and the reaction medium is passing through the catalyst bed in the reactor. In certain embodiments, the applicants apply a liquid hourly space velocity (LHSV) in the range of 0.05 to 10 kg/h per litre of catalyst bed, at least 0.10, at least 0.20, at least 0.25, at least 0.30, at least 0.50, at least 0.75, at least 1.00, at least 2.00, at least 4.00, or at least 5.00 kg/h per litre of catalyst bed kg/h per litre of catalyst bed. Optionally in certain embodiments, the LHSV is at most 500 kg/h per litre of catalyst bed, at most 100, at most 50, at most 10 kg/h per litre of catalyst bed, at most 8.0, at most 7.0, at most 6.0, at most 5.0, at most 4.0, or at most 3.0 kg/h per litre of catalyst bed.

In an embodiment of the process according to the present invention wherein the catalyst is heterogeneous, the heterogeneous catalyst comprises a first metal on a solid support.

In certain embodiments of the process according to the present invention, the heterogeneous catalyst comprises the first metal at a concentration in the range of 0.1-40.0% by weight, at a concentration of at least 0.5% by weight, at least 1.0%, at least 1.5%, at least 2.0%, at least 2.5% by weight, at least 3.0%, at least 3.5%, at least 4.0%, at least 4.5% by weight, or at least 5.0% wt, and optionally at a concentration of at most 35.0% wt, at most 30.0% wt, at most 20.0% wt, at most 10.0% wt, at most 9.0% wt, at most 8.0% wt, at most 7.0% wt, at most 6.0% wt, at most 5.0%, or at most 4.0%, all based on the total weight of the catalyst. The applicants have found that these levels provide an advantageous balance between catalyst performance and the costs and efforts associated with the production of the catalyst. The catalyst comprising the first metal may be monometallic, bimetallic, or multimetallic.

In an embodiment, the process according to the present invention further comprises the step of putting a first metal onto a support by precipitation. The applicants have found that the precipitation method is a very convenient method for putting a metal such as palladium onto a support. Suitable precipitation methods for putting palladium metal onto a support are well known in the art.

In certain embodiments of the process according to the present invention, the heterogeneous catalyst has a metal area, as measured by carbon monoxide chemisorption of at least 0.5 m2/g, at least 1.0 m2/g, at least 2.0 m2/g, at least 3.0 m2/g, or at least 4.0 m2/g, optionally at most 12.0 m2/g.

In certain embodiments of the process according to the present invention, the heterogeneous catalyst has an average metal particle size in the range of 0.5 nm to 20 nm, at least 1.0 nm, at least 1.5 nm, at least 2.0 nm, at least 3.0 nm, or 4.0 nm, optionally at most 20.0 nm, at most 15.0 nm, at most 12.0 nm, at most 10.0 nm, at most 9.0 nm or even at most 8.0 nm. The average metal particle size is preferably measured using X-ray powder diffraction (XRPD), whereby the applicants prefer to use the Sherrer equation based on half-peak width.

In certain embodiments of the process according to the present invention, the heterogeneous catalyst has a support selected from the list consisting of carbon, alumina, silica, zeolite, clay, porous polymer and hybrid polymer, a carbon support, an activated carbon, or an activated carbon which has been activated by a treatment with an acid. The applicants have found that the heterogeneous catalyst on a carbon support is particularly sensitive to any heat treatment or pre-reduction step according to the present invention, and that such catalyst is also particularly effective in obtaining the desired effect of the present invention. The applicants have also found that with a carbon support, the initial by-product formation may be slightly higher than with other supports, such as silicium oxide (silica) or an aluminium oxide (alumina). The applicants have found however that, with the silica or alumina support, the catalyst behaviour is less stable. The applicants have observed that the catalyst can deactivate faster and the reaction time needed for obtaining the same target conversion can increase, whereby more of the potentially undesirable dimer by-product is formed. The carbon support thus brings the advantage of a higher catalyst stability, which results over time in the combination of a shorter reaction time and a lower formation of the potentially undesirable by-product.

For the ease of handling, the catalyst is in one embodiment supported on a solid carrier. A suitable carrier for the support of the metals in the catalyst of the process according to the present invention is activated carbon, because of its large specific surface area and its good adhesion properties. Further treatment, such as steaming, acid washing, sulphonation, or the like, may be given to the support, because this often enhances the adsorption properties of the activated carbon. Other carbon carriers such as graphite or carbon nanotubes (CNT) may be used as the support of the catalyst. Carbon supports offer the additional advantage that the process for recycling the metal or metals, at the end of life of the catalyst, is much simplified as compared with other supports.

Other types of materials known by people skilled in the art may suitably be used as the catalyst support: alumina, silica, zeolite, clay, porous polymer and hybrid polymer, and combinations thereof.

The supported catalyst may occur in a form which is most suitable and desired for the process, such as a powder, in the form of a granule, an extrudate, or combinations thereof. With a powder catalyst, the catalyst may after use be separated from the reaction mixture by filtration. With granules and/or extrudates, the catalyst and the reaction mixture may be separated from each other by simple draining of the reactor vessel containing the catalyst, which may for instance be arranged in a fixed bed arrangement.

In an embodiment of the process according to the present invention, the heterogeneous catalyst is a bimetallic catalyst. In certain embodiments, the heterogeneous catalyst comprises at least one first metal selected from the list consisting of palladium, Pd, platinum, Pt, rhodium, Rh, iridium, Ir, and ruthenium, Ru, together with at least one second metal selected from the list consisting of silver, Ag, nickel, Ni, cobalt, Co, iron, Fe, tin, Sn, lead, Pb, bismuth, Bi, gold, Au, and copper, Cu. The applicants have found that this catalyst is particularly suitable for performing the reductive amination reaction according to the present invention, and for achieving the desired effects thereof in terms of selectivity, activity, suppression of dehalogenation, as well as suppression of the formation of the potentially undesirable by-product which is the target of the present invention.

In certain embodiments of the process according to the present invention wherein the catalyst is bimetallic, the heterogeneous catalyst comprises the second metal at a concentration in the range of 0.05-40% by weight, based on the total weight of the catalyst, at a concentration of at least 0.1% by weight, at least 0.5%, at least 1.0% wt, at least 1.5% wt, at least 2.0% by weight, at least 3.0% wt, at least 4.0% wt, at least 4.5% by weight, at least 5.0% by weight, at least 5.5% wt, or at least 6.0% by weight, and optionally at a concentration of at most 35.0% by weight, at most 30.0% wt, at most 25.0% wt, at most 20.0% wt, at most 18.0% wt, at most 16.0% wt, at most 14.0% wt, at most 12.0% wt, at most 10.0% wt, at most 9.5%, at most 9.0% wt, at most 8.5% wt, at most 8.0% wt, at most 7.5% wt, at most 7.0% wt, or at most 6.5% wt, all based on the total weight of the catalyst. The applicants have found that these levels of the second metal are also bringing an advantageous compromise between the performance of the catalyst in the process and the complexity and efforts in the production of the catalyst.

In certain embodiments of the process according to the present invention wherein the catalyst is bimetallic, the heterogeneous catalyst comprises the first metal and the second metal in a weight ratio of the second metal relative to the first metal in the range of 0.05:1.0 to 10.0:1.0, at least 1.0:1.0, at least 2.0:1.0, or at least 3.0:1.0. The applicants have found that this brings the advantage of a further suppression of the undesired side reaction forming the potentially undesirable by-product.

In an embodiment of the process according to the present invention wherein the catalyst is bimetallic, the process further comprises the step of putting the second metal onto a support by precipitation, at the same time as putting the first metal onto the support or after having put the first metal onto the support. The applicants have found that this is a most convenient way of producing the bimetallic catalyst suitable for use in the process of the present invention.

In an embodiment of the process according to the present invention, the heterogeneous catalyst is rather monometallic. In certain embodiments, the heterogeneous monometallic catalyst comprises at least one first metal selected from the list consisting of palladium, Pd, platinum, Pt, rhodium, Rh, iridium, Ir, and ruthenium, Ru, and the catalyst is in absence of a catalytic amount of any second metal selected from the list consisting of silver, Ag, nickel, Ni, cobalt, Co, tin, Sn, bismuth, Bi, copper, Cu, gold, Au and combinations thereof, whereby the heterogeneous catalyst has been heat-treated prior to the reductive amination at a temperature in the range of 100° C. to 600° C. for a period of at least two hours.

In one embodiment, the first metal can be selected from the list consisting of palladium, Pd, platinum, Pt, rhodium, Rh, iridium, Ir, and ruthenium, Ru. In one embodiment, palladium or platinum can be selected as the first metal. Palladium and platinum can be more readily available than most of the other noble metals in the list of first metals, and can therefore be more readily obtainable as a raw material, usually also at a lower cost for the production of the catalyst. Palladium and platinum can also be easier to recover or to recuperate from a spent catalyst, and to recycle into a new use. Although palladium and platinum are typically not recognized as highly selective catalysts for performing reductive aminations of substrates containing halogens it has been found that the catalysts containing palladium or platinum as the first metal, and in absence of the second metal as specified above, when properly heat treated according to the present invention, can surprisingly combine the benefits of a high activity with a greatly improved selectivity when reacting halogen containing substrates. In one embodiment, this advantage can extend also to the other first metals, as specified. Ruthenium may further be advantageous to use as a first metal, because it is also more readily available as compared to some other first metals. One advantage is that is usually also available at a somewhat lower cost.

In an embodiment, the applicants use a monometallic catalyst for the process according to the present invention, whereby is meant a catalyst comprising only catalytic amounts of the at least one first metal. We have also found that such a monometallic catalyst is easier to obtain as compared to bimetallic catalysts. Bimetallic catalysts, or catalysts with even more different metals, typically require at least two steps for depositing the metals on the catalyst. With bimetallic catalysts, or catalyst containing even more different metals, whereby the different metals should collaborate with each other in order to obtain the desired catalytic benefits, it is also usually more critical that the metals have the desired distribution over the support surface of the catalyst, and also that the deposits of the different metals are sufficiently close to each other to enable the catalytic cooperation between the two metals. The applicants have found that the catalysts containing only catalytic amounts of the first metals, whereby there is no cooperation between different metals required in order to obtain the desired effect, are easier to obtain as compared to the catalysts requiring the presence of also second metals in catalytic quantities in order to achieve the desired catalytic effects. Furthermore, such single metal or monometallic catalysts may often have a lower risk of metal leaching, and the metal may be more easily recovered and refined from the spent catalyst. Another advantage of monometallic catalysts over bimetallic catalysts is that they may be manufactured with a higher reproducibility.

We have found that also with these monometallic catalysts, the process according to the present invention can also be highly selective in performing the desired chemical conversion of the first functional group, while keeping the further functional group containing the halogen atom substantially intact such that the halogen remains present in the reaction product.

We have found that the dehalogenation of a halide function as the further functional group on the substrate, a side reaction which is occurring when using monometallic palladium catalyst, may be significantly suppressed, and essentially avoided, when using the heat treated and/or bimetallic catalyst as disclosed above. The dehalogenated by-product is potentially undesirable. The same may apply to the halide containing by-product (e.g. HX) of the undesired dehalogenation reaction, which for instance may cause corrosion to the reactor or downstream processing equipment. The side reaction thus typically represents a downgrade of valuable starting materials, and adds additional burden for removal of the by-products from the desired reaction product or for selecting more precious construction materials.

The process using the catalysts as prescribed elsewhere in this document thus brings the advantage of producing a highly pure desired reaction product, which requires much less clean-up, if any, before it may be put to further use. The process also brings the advantage of highly efficient use of the starting organic substrate, with very low downgrade, if any, to by-products which may be undesired in the prime reaction product, in which case the by-products must be separated off and typically discarded or even require additional efforts for disposal in a responsible manner. Furthermore, the process according to the present invention may avoid the use of expensive and generally less active platinum as the metal in the catalyst without compromising the selectivity.

The process according to the present invention is performed in the presence of hydrogen. The use of hydrogen (H2) as the reducing agent is much favoured by the presence of a metal catalyst. Such a catalyst is believed to be instrumental in activating the molecular hydrogen by weakening the H—H bond. Next to the activation of H2, the catalyst may also play a role in other reaction steps, such as the other steps involved in the reductive amination mechanism. This role together with the characteristics of the reaction conditions (such as the presence of free amine, water, the typical temperature and pressure range, etc.) make that reductive amination catalysts are often tailored for this specific process, especially when sensitive (e.g. multifunctional) substrates are involved. It was therefore surprising to see that a heat treated monometallic catalyst was found to show such good halogen retention properties.

In an embodiment, the current invention involves the use of a heat treated Pd catalyst for the reductive amination of halogenated substrates in the presence of hydrogen. Being a catalytically very active metal, Pd has the advantage over Pt of being much cheaper and being easier to recover.

In certain embodiments of the process according to the present invention using a monometallic catalyst, the heterogeneous catalyst comprises the second metal or combinations thereof at a concentration of at most 0.1% by weight, based on the total weight of the catalyst, at most 0.05% by weight, at most 0.01% by weight, or at most 0.005% by weight.

In certain embodiments of the process according to the present invention using a heat treated catalyst, the heterogeneous catalyst has been heat treated, such as prior to its use in the process, at a temperature in the range of at least 200° C., at a temperature of at least 250° C., at a temperature of at least 300° C., at least 350° C., or at least 400° C., and optionally at a temperature of at most 550° C., at most 500° C., or at most 450° C., the heat treatment being performed for at least 1 hour, 2 hours, at least 3 hours, at least 4 hours, at least 5 hours, at least 6 hours, at least 7 hours, or at least 8 hours, and for at most 24 hours, at most 18 hours, at most 12 hours, at most 10 hours, at most 8 hours, at most 6 hours, at most 5 hours, at most 4 hours, or at most 3 hours. In one embodiment, one heat-treats the catalyst at about 400° C., in nitrogen, for a period of about 2 hours with a N2 flow at a velocity expressed as weight/weight/hour (WWH) of about 0.225-0.250 per hour (h-1), and this after first having dried the catalyst at about 80° C. for a period of 3 hours, in stagnant air or under a flow of gas to remove water vapour, i.e. until no substantial further weight loss of the catalyst being dried could anymore be noticed.

In an embodiment of the process according to the present invention using a heat treated catalyst, the atmosphere during the heat treatment is a gaseous atmosphere, and in one embodiment selected from hydrogen H2, nitrogen N2, an inert gas and air.

In certain embodiments of the process according to the present invention using a heat treated catalyst, the heat treatment of the heterogeneous catalyst has been performed by exposure to a flow of gas at a WWH in the range of from 0.0200 to 2.0000 $h^{-1}$, at least 0.0375 $h^{-1}$, at least 0.050 $h^{-1}$, at least 0.075 $h^{-1}$, at least 0.120 $h^{-1}$, at least 0.150 $h^{-1}$, at least 0.200 $h^{-1}$, or at least 0.220 $h^{-1}$, and optionally at most 1.500 $h^{-1}$, at most 1.000 $h^{-1}$, at most 0.500 $h^{-1}$, or at most 0.300 $h^{-1}$. The applicants have found that the heat-treatment under these conditions is particularly convenient but also particularly effective in obtaining the technical effects which are the target of the present invention.

In certain embodiments of the process according to the present invention using a heat treated catalyst, the heterogeneous catalyst at the start of the heat-treatment contained at most 10% wt of free water, at most 8% wt of free water, at most 5% wt of free water, at most 3.0% wt of free water, at most 2.0% wt of free water, or at most 1.0% wt of free water, and optionally at least 0.01 wt % free water. The applicants have found that this feature reduces the risk that the heterogeneous catalyst becomes damaged during the heat-treatment step. Free water is defined in this context as the water which may be removed by drying at a temperature of at most 100° C., as observed by weight loss.

In an embodiment of the process according to the present invention using a heat treated catalyst, the heterogeneous catalyst has been dried prior to the heat-treatment. The applicants have found that a drying step is a very convenient step in order to achieve a limited free water content of the heterogeneous catalyst, which was found to bring the advantage of reducing the risk that the heterogeneous catalyst becomes damaged during the heat-treatment step. A drying step is defined in this context as an heating of the catalyst to a temperature of less than 100° C. for a period of time suitable for removing the desired amount of free water, as measurable by weight loss. The drying step may be performed using a heated gas flow to remove vaporising water. The drying step may be performed separate from the heat treatment step, or may be performed during the starting phase of the heat treatment step, for instance by keeping the catalyst under a gas flow at the prescribed temperature for a suitable time before the temperature is raised for starting the heat treatment. The applicants have found that this last combination of drying step and heat treatment step is particularly convenient for implementation at a commercial scale.

In an embodiment of the process according to the present invention using a heat treated catalyst, the heat treatment is made in the presence of a liquid selected from the feed substrate, a solvent, and mixtures thereof. In one embodiment the substrate is in the liquid form. The applicants have found that the use of a liquid during the heat treatment is a very convenient way to bring heat energy into the heterogeneous catalyst which is solid. The applicants have found that transferring heat to a solid by use of a liquid is much more effective than by using only a gaseous carrier for introducing the heat energy.

In certain embodiments of the process according to the present invention, the heterogeneous catalyst has been pre-reduced prior to the step of contacting the catalyst with the organic feed substrate, by subjecting the catalyst at a temperature of at least 120° C., or at least 140° C. to a hydrogen atmosphere of at least 5 bar gauge, or at least 8 bar gauge during a period of at least 30 minutes, at least 45 minutes, the pre-reduction being performed with the catalyst being in contact with an organic liquid phase, such as an alkanol, or, for example, methanol. The applicants prefer to perform this pre-reduction step with the catalyst in contact with methanol, at a temperature of about 150° C., and under a hydrogen partial pressure of about 10-11 bar absolute, and this for a period of about three hours. Alternatively, the applicants may perform the pre-reduction step with the catalyst in contact with methanol at a temperature of about 180° C., and under a hydrogen partial pressure of about 10-11 bar absolute, and this for a period of about one hour.

In another embodiment of the process according to the present invention comprising a pre-reduction step, the pre-reduction is performed in the presence of a solvent, such as methanol, or in one embodiment only in presence of the solvent. In yet another embodiment, the pre-reduction is performed in presence of the nitrogen containing compound, also in the presence of the solvent, for example, is methanol, in mixture with and/or as a solvent for the nitrogen containing compound. In one embodiment, applicants perform the pre-reduction in order to obtain an improved effect. Practical limitations however may make it preferable to perform the pre-reduction in the presence of the nitrogen-containing compound, in which case there may or may not be a solvent present.

The applicants have found that this pre-reduction step allows the catalyst to exhibit its desired advantageous performance from very early on after starting the process. The applicants have further found that this pre-reduction also contributes in suppressing the formation of the potentially undesirable by-product dimer.

In certain embodiments of the process according to the present invention, at least 80% of the feed substrate is retaining the at least one further functional group after the conversion, at least 85%, at least 90%, at least 95%, at least 97%, at least 98%, at least 99.0%, at least 99.4%, at least 99.5%, or at least 99.6% of the feed substrate is retaining the at least one further functional group after the conversion. The applicants have found that these results are readily achievable with the catalyst of the process according to the present invention.

In an embodiment of the process according to the present invention, the reductive amination and/or the catalyst heat treatment step, is performed in the presence of a solvent, for example, an organic solvent, the organic solvent being hydrophilic and aprotic, such as tetrahydrofuran, diethylether, methyl tertiary butyl ether, or 1,4-dioxan, and in one embodiment, the solvent comprises at least one alkanol, for example methanol, the solvent being present in certain embodiments in a weight ratio relative to the organic feed substrate in the range of 0.1-20 g/g, at least 0.2 g/g, or at least 0.3 g/g, optionally at most 15.0 g/g, at most 10.0 g/g, at most 5.0 g/g, at most 4.0 g/g, at most 3.0 g/g, at most 2.0 g/g, or at most 1.0 g/g. Reductive amination reaction and/or the heat treatment step, according to the process of the present invention may occur in any suitable medium. Solvents such as water, alcohols (e.g. methanol), tetrahydrofuran (THF), dioxane, alkanes may be used advantageously. A solvent may bring advantages to such reductive amination reaction, such as an improved hydrogen solubility, a decreased viscosity of the reaction mixture, an improved mixing efficiency, an improved heat transfer, etc. The concentration of the substrate and products in such solvents may in certain embodiments be between 1 and 50%, between 5 and 40%, or between 10 and 40% by weight, based on the total reaction mixture. Highly diluted reaction mixtures may result in poor space-time yields, while in case of highly concentrated reaction mixtures, the benefits of the solvent may be minimized. In case the reaction substrates and products are liquids under the reaction conditions applied, the reaction may be performed without the addition of a solvent. One may also choose to add small amounts of solvents to the reaction mixture, e.g. 1 to 50%, 5 to 40%, or 10 to 30% by weight, relative to the total reaction mixture. Such addition may have particular advantages such as to improve the catalyst performance, to decrease the autogenous pressure of the reaction mixture, to prevent phase separation to occur, etc.

In case of the reductive amination of o-chloro benzaldehyde with dimethyl amine (DMA), we have found that the addition of small amounts of methanol to the reaction mixture improves the yield and operability of the process significantly. Without wanting to be bound by this theory, the methanol is believed to increase the solubility of the highly volatile amine and therefore enhancing the reaction rate in the liquid phase. Additionally, the presence of methanol may possibly prevent the occurrence of two separate liquid phases during the reductive amination, possible because of any liberation of water as the co-product in the reaction.

In an embodiment, the process according to the present invention further comprises the purification of the converted substrate, for example by the distillation of the reaction product, for reducing the content of at least one compound selected from a reaction by-product, a feed impurity, a solvent, and unreacted feed substrate.

In an embodiment the process according to the present invention is used for the production of ortho-chloro benzyl dimethyl amine, 2-Cl-BDMA. In such an embodiment the process optionally further comprises subjecting the 2-Cl-BDMA to a Grignard reaction, comprising for example in a first step the preparation of a Grignard reagent in which a magnesium atom is introduced in between the benzene ring and the chlorine atom, followed by a second step wherein the Grignard reagent is reacted with an oxalic acid dialkyl ester.

The o-Cl-BDMA produced by the process according to the present invention is particular useful if further reaction steps to form further derivatives comprise metallation reactions such as lithiation or Grignard reactions, such as described in US 2010/0113778 A1, or coupling reactions such as the reactions known as the Heck, the Sonogashira, the Suzuki or the Stille coupling.

In an embodiment, the process according to the present invention further comprises the production of a methoximinophenylglyoxylic ester, preferably further including the production of a fungicide including the methoximinophenylglyoxylic ester.

In an embodiment wherein the process according to the present invention comprises the production of a fungicide including the methoximinophenylglyoxylic ester, the process further includes the step of treating a surface with the fungicide containing the methoximinophenylglyoxylic ester.

In certain embodiments of the present invention, the composition comprises at most 0.50% wt of the meso-o-Cl-BDMA dimer, at most 0.40% wt, at most 0.30% wt, at most 0.25% wt, at most 0.20% wt, at most 0.15% wt, at most 0.10% wt, at most 500 ppm wt, at most 250 ppm wt, at most 100 ppm wt, at most 50 ppm wt, at most 10 ppm wt, or at most 5 ppm wt of the meso-o-Cl-BDMA dimer, based on the total weight of the composition. The applicants have found that the lower the presence of the meso-o-Cl-BDMA dimer, the lower the risk for operational problems. The applicants have further found that the lower the concentration of the meso-o-Cl-BDMA dimer in the reaction medium, the lower any effect this potentially undesirable compound may have on the catalyst performance. The applicants have found that at lower concentrations, in particular when the concentration of the meso-o-Cl-BDMA dimer is below 0.25% wt in the reaction medium, that any possible deterioration of catalyst activity and/or selectivity, which may be noticeable at higher levels, become sufficiently low in order to be operationally and commercially acceptable.

In certain embodiments of the present invention, the composition comprises at least 5 ppm wt the meso-o-Cl-BDMA dimer, at least 10 ppm wt, at least 20 ppm wt, at least 30 ppm wt, at least 50 ppm wt, at least 100 ppm wt, at least 0.10% wt, at least 0.20% wt, at least 0.25% wt, at least 0.30% wt, at least 0.40% wt, or at least 0.50% wt of the meso-o-Cl-BDMA dimer, based on the total weight of the composition.

In certain embodiments of the present invention, the composition comprises at least of 5 ppm wt of the dl-o-Cl-BDMA dimer, at least 10 ppm wt, at least 20 ppm wt, at least 30 ppm wt, at least 50 ppm wt, at least 100 ppm wt, at least 250 ppm wt, at least 500 ppm wt, at least 0.10% wt, at least 0.15% wt, at least 0.20% wt, at least 0.25% wt, at least 0.30% wt, at least 0.40% wt, or at least 0.50% wt of the (+/−)-o-Cl-BDMA dimer, based on the total weight of the composition. The applicants have found that these concentrations of the (+/−)-o-Cl-BDMA dimer can be present in the composition without jeopardising or affecting the performance of the composition in many of its applications, such as particular conversions into further chemical derivatives, in particular those conversions and uses which have been described in more detail elsewhere in this document The applicants have found that, for many of such applications, there is little to no need for the removal of any (+/−)-o-Cl-BDMA dimer which may be present in the composition, in particular not when it is present at the levels as specified. This represents an advantage because the removal of (+/−)-o-Cl-BDMA dimer from the prime product 2-chloro-benzyl-dimethylamine, and this to very low levels, may bring significant additional complexity to the process.

In certain embodiments of the present invention, the composition comprises at most 0.50% wt of the (+/−)-o-Cl-BDMA dimer, at most 0.40% wt, at most 0.30% wt, at most 0.25% wt, at most 0.20% wt, at most 0.15% wt, at most 0.10% wt, at most 500 ppm wt, at most 250 ppm wt, at most 100 ppm wt, at most 50 ppm wt, at most 10 ppm wt, or at most 5 ppm wt of the (+/−)-o-Cl-BDMA dimer, based on the total weight of the composition.

In certain embodiments of the composition according to the present invention, the composition comprises at least 98.5% wt of 2-chloro-benzyl-dimethylamine, at least 99.0% wt, at least 99.1% wt, at least 99.2% wt, or at least 99.3% wt of 2-chloro-benzyl-dimethylamine. The higher the content in 2-chloro-benzyl-dimethylamine, the more advantageously the composition may be applied in its desired application, such as a conversion to a further chemical derivative.

In certain embodiments of the composition according to the present invention, the composition comprises at least 0.005% wt (50 ppm by weight) of 2-chloro-benzyl alcohol, at least 0.007% wt of 2-chloro-benzyl alcohol, at least 0.009% wt, at least 0.010% wt, at least 0.012% wt, at least 0.015% wt, at least 0.020% wt, at least 0.030% wt, at least 0.040% wt, at least 0.05% wt, at least 0.07% wt of 2-chloro-benzyl alcohol, at least 0.09% wt, at least 0.10% wt, at least 0.12% wt, or at least 0.15% wt of 2-chloro-benzyl alcohol.

In certain embodiments of the process according to the present invention, the composition produced by the reductive amination comprises at most 0.04% wt of 2-chloro-dichloromethyl benzene, at most 0.030% wt, at most 0.020% wt, at most 0.015% wt, at most 0.010% wt, at most 50 ppm by weight, or at most 10 ppm, of 2-chloro-dichloromethyl benzene. This component may represent an additional burden in applying the composition, such as generating corrosive components in subsequent reactions, and/or leading to potentially undesirable by-products in subsequent conversions. The lower the content of 2-chloro-benzylchloride, the more advantageously the composition may be applied in its desired application, such as a conversion to a further chemical derivative.

In certain embodiments of the process according to the present invention, the composition produced by the reductive amination comprises at most 1.0% wt of 2-chloro-benzyl alcohol, at most 0.80% wt, at most 0.60% wt, at most 0.50% wt, or at most 0.40% wt of 2-chloro-benzyl alcohol.

The applicants have found that the 2-chloro-benzyl alcohol can be present in the composition without jeopardising or affecting the performance of the composition in many of its applications, such as particular conversions into further chemical derivatives, in particular those conversions and uses which have been described in more detail elsewhere in this document. The applicants have found that there is, for many of such applications, little to no need for the removal of any 2-chloro-benzyl alcohol which may be present in the composition, in particular not when it is present at the levels as specified. This represents an advantage because the removal of 2-chloro-benzyl alcohol from the prime product 2-chloro-benzyl-dimethylamine, and this to very low levels, may bring significant additional complexity to the process.

In certain embodiments of the process according to the present invention, the composition produced by the reductive amination comprises at most 0.20% wt of 2-chloro-benzaldehyde, at most 0.15% wt, at most 0.10% wt, at most 0.05% wt, at most 0.020% wt, at most 0.010% wt, at most 50 ppm by weight, at most 10 ppm, at most 5 ppm, or at most 1 ppm by weight, as determined by gas chromatography, GC, if needed assisted by mass-spectrometry. This 2-chloro-benzaldehyde does not contribute to many of the applications of the composition. A presence at a lower level of this component therefore represents an improved effectiveness and brings improved efficiencies in the further use and application of the composition.

In certain embodiments of the process according to the present invention, the composition produced by the reductive amination comprises at most 0.40% wt of 4-chloro-benzyl dimethylamine, at most 0.30% wt, at most 0.20% wt, at most 0.10% wt of 4-chloro-benzyl dimethylamine, at most 0.05% wt, at most 0.020% wt, at most 0.010% wt, at most 50 ppm by weight, at most 10 ppm, at most 5 ppm, or at most 1 ppm by weight, as determined by gas chromatography, GC. The applicants have found that this component may represent an additional burden in applying the composition, such as in subsequent reactions, and/or may lead to potentially undesirable by-products in subsequent conversions which in addition may be rather difficult to separate from the desired product of such conversion. The lower the content of 4-chloro-benzyl dimethylamine, the more advantageously the composition may be applied in its desired application, such as a conversion to a further chemical derivative.

In certain embodiments of the process according to the present invention, the composition produced by the reductive amination comprises at most 0.40% wt, at most 0.35% wt of ortho-chloro toluene, at most 0.30% wt, at most 0.20% wt, at most 0.10% wt of ortho-chloro toluene, at most 0.05% wt, at most 0.03% wt, at most 0.01% wt, at most 0.05% wt, at most 0.020% wt, at most 0.010% wt, at most 50 ppm by weight, at most 10 ppm, at most 5 ppm, or at most 1 ppm by weight, as determined by gas chromatography, GC. These specified % wt. levels apply to the total weight of all chloro toluene isomers. The applicants have found that this component, and also its isomers, may represent an additional burden in applying the composition, such as in subsequent reactions, and/or may lead to potentially undesirable byproducts in subsequent conversions which in addition may be rather difficult to separate from the desired product of such conversion. The lower the content of chloro toluenes, in particular of ortho-chloro toluene, the more advantageously the composition may be applied in its desired application, such as a conversion to a further chemical derivative.

In certain embodiments of the process according to the present invention, the composition produced by the reductive amination comprises at most 0.40% wt of benzyl dimethyl amine, at most 0.30% wt, at most 0.20% wt, at most 0.10% wt of benzyl dimethyl amine, at most 0.05% wt, at most 0.020% wt, at most 0.010% wt, at most 50 ppm by weight, at most 10 ppm, at most 5 ppm, or at most 1 ppm by weight, as determined by gas chromatography, GC. This benzyl dimethyl amine does not contribute to many of the applications of the composition. A presence at a lower level of this component therefore represents an improved effectiveness and brings improved efficiencies in the further use and application of the composition.

In certain embodiments of the process according to the present invention, the composition produced by the reductive amination comprises at most 0.40% wt of 2-dimethylamino-benzyl dimethylamine, at most 0.30% wt, at most 0.20% wt, at most 0.10% wt of 2-dimethylaminobenzyl dimethylamine, at most 0.05% wt, at most 0.020% wt, at most 0.010% wt, at most 50 ppm by weight, at most 10 ppm, at most 5 ppm, or at most 1 ppm by weight, as determined by gas chromatography, GC. This 2-dimethylamino-benzyldimethylamine does not contribute to many of the applications of the composition. A presence at a lower level of this component therefore represents an improved effectiveness and brings improved efficiencies in the further use and application of the composition.

In certain embodiments of the process according to the present invention, the composition produced by the reductive amination comprises at most 0.40% wt of benzaldehyde, at most 0.30% wt, at most 0.20% wt, at most 0.10% wt of benzaldehyde, at most 0.05% wt, at most 0.020% wt, at most 0.010% wt, at most 50 ppm by weight, at most 10 ppm, at most 5 ppm, or at most 1 ppm by weight, as determined by gas chromatography, GC. This benzaldehyde does not contribute to many of the applications of the composition. A presence at a lower level of this component therefore represents an improved effectiveness and brings improved efficiencies in the further use and application of the composition.

The applicants have found that the process according to the present invention is particularly suitable, because the process is able to provide a high reaction rate and conversion to the desired 2-chloro-benzyl-dimethylamine, which achieves low levels of the unconverted feed substrate 2-chloro-benzaldehyde, and thanks to the high selectivity of the catalyst as described, with low presence of less desired by-products, such as 2-chloro-benzyl alcohol and/or benzyl dimethyl amine and/or 2-dimethylamino-benzyldimethylamine. In addition, the process according to the present invention for the production of 2-chloro-benzyl-dimethylamine has little to no presence of the other potentially undesirable components 2-chloro-benzylchloride and/or 4-chloro-dimethylbenzylamine and/or chloro toluene isomers, in particular ortho-chloro toluene. The composition obtainable by the process according to the present invention is thus particularly suitable for use in many of its applications, such as particular conversions into further chemical derivatives, in particular those conversions and uses which have been described in more detail elsewhere in this document.

In an embodiment wherein the process according to the present invention is used for the production of ortho-chloro benzyl dimethyl amine, 2-Cl-BDMA, the process is further comprising the conversion of 2-Cl-BDMA into o-chloromethylphenylglyoxylic esters by a method such as described in US 2010/113778 A1. o-Chloro-methyl-phenylglyoxylic esters are important intermediates for preparing agrochemically active compounds or microbicides of the methoximinophenylglyoxylic ester series. More particularly, US 2010/113778 A1 describes the production of strobilurines, a type of fungicides that are stated to inhibit the respiratory system of the fungi, and of which Kresoxim-methyl and Dimoxystrobin are named and exemplified as particularly interesting family members. In a further embodiment therefore, the process according to the present invention further comprises the production of a fungicide containing a methoximinophenylglyoxylic ester derivatized from 2-Cl-BDMA, in particular derived from the composition according to the present invention.

In an embodiment wherein the process according to the present invention is used for the production of ortho-chloro benzyl dimethyl amine, 2-Cl-BDMA, the process is further including the step of treating a surface of a substrate with the fungicide containing the methoximinophenylglyoxylic ester which was derived from the 2-Cl-BDMA obtained with the reductive amination. Such a surface may be from, but is not limited thereto, an agricultural field, an orchard, a leaf or stem of an agricultural crop, a slab, a floor tile, a façade, a wall or a roof of a building, a cardboard box or any other kind of packaging material, a portion of human skin, of human mucosa, of animal skin, or of animal mucosa. The fungicide composition may be a solid, such as a powder, or a liquid, in which the ester may be dissolved or dispersed in a carrier or solvent. The process of using the fungicide composition may be performed using any one of the methods known in the art, and combinations thereof, such as by spraying, by brushing, by pouring, by dusting, by mixing and the like, including combinations thereof.

As used throughout the present application, the term "wt %", refers to percentage by weight, the term "ppm wt." refers to weight in ppm, and the terms "wt." and "wt" both refer to weight.

Analyticals

For analysing the composition produced by the process according to the present invention, as well as in the monitoring of the process according to the present invention, the applicants prefer to use the following gas chromatography, GC, analytical method.

The GC apparatus is preferably an Agilent 6890N with split injector and a flame ionization detector (FID). The apparatus is equipped with a capillary column coated with a stationary phase type CP-Sil 5 CB with dimensions 60 m×320 μm×5.0 μm. The applicants prefer to use an injector temperature of 280° C., an injector volume of 1 μlitre and a split ratio of 1/30. The applicants prefer to use helium as the carrier gas, with a flow of 2 ml/min at constant flow. The oven is given a temperature program of holding for 3 minutes at 60° C., and subsequently ramping up the temperature at a rate of 20° C. per minute up to 290° C., at which temperature the column is kept for an additional 15 minutes. The FID detector is kept at 300° C., and fed with a hydrogen flow of 45 ml/min and an air flow of 450 ml/min. Make up gas, for example nitrogen, and column flow together are set at a total of 45 ml/min.

The applicants have found that the following components may readily be identified by specific retention peaks: methanol, DMA, TMA, ethylbenzene, benzaldehyde, benzyl dimethyl amine, ortho-chloro benzaldehyde, ortho-chloro benzylalcohol, ortho-chloro benzyl dimethyl amine, para-chloro benzyl dimethyl amine, ortho (dimethylamino) benzyl dimethyl amine. The applicants have further found that this GC technique may readily be assisted with the addition of mass-spectrometry, such as for determining concentrations in the lower levels, which for many of the compounds is down to 1 ppm wt or possibly even below.

Depending on the sample, the sample may be diluted up to 10 times in isopropanol. In one embodiment 1% of the internal standard is added, upon which the sample is for example vigorously mixed for at least one minute, and after which 1 µl of sample may be injected into the gas chromatograph.

The peaks representing the two o-Cl-BDMA dimers were identified using GCMS and NMR. In this analysis, the GC was performed as follows:

Inlet: Injector temperature: 350° C.
  Injector volume: 1 µl
  Split ratio 1/35
Column: HP-5 (5% Phenyl Methyl Siloxane): 30 m×320 µm×0.25 µm
  Carrier gas: Hydrogen
  Flow: 2 ml/min
  Constant flow
Oven: 80° C. —1 minute
  10 degrees C. per minute, up to 280° C., remaining for 3 minutes
Detector: Type: FID
  Detector temperature: 350° C.
  Hydrogen flow: 30 ml/min
  Air flow: 330 ml/min
  Make up (helium)+column flow: 20 ml/min.

With this GC parameters and column, one of the o-Cl-BDMA dimers had a retention time of 15.43 minutes and the second dimer had a retention time of 15.89 minutes. The two peaks were thus quite distinct from each other. The two peaks could be identified because both their mass spectra were identical, and showed one important fragmentation towards m/z 168, which is the exact half of the dimer, a fragmentation which is expected from the dimer structure. The molecular mass was 336 and the first logical loss (−15 to fragment 321) could also be seen. Another fragment at 292 was also found (loss of 44), and was attributed to the loss of a dimethyl amino group. When fragment 168 loses this dimethyl amino group, it yields a fragment 125, which also showed up in both mass spectra.

The applicants synthesized in the lab the dimerization product of o-Cl-BDMA and subjected the resulting mixture to NMR analysis. This analysis demonstrated that three stereoisomers were formed—the (+/−)-o-Cl-BDMA dimer pair and the meso-o-Cl-BDMA dimer. Using a synthesis method that is stereospecific, the applicants were able to synthesize the meso-o-Cl-BDMA dimer isomer in relatively high purity. The composition of this synthesis product was confirmed by NMR analysis. The retention time of this isomer in the above GC analysis was subsequently identified, whereby the two peaks representing the respective isomers of the dimer could be identified in the GC(MS) spectrum. It was found that in the above GC method, the meso-o-Cl-BDMA dimer had the longest retention time of the stereoisomers.

EXAMPLES

Example 1: Preparation of the Pd/Cu on Carbon Catalyst

A catalyst comprising 3% wt Pd and 7% wt Cu on carbon, was prepared by slurrying a 3% wt Pd/C catalyst in demineralised water. Then, an appropriate amount of $CuCl_2$ aqueous solution was added to the slurry. Subsequently, aqueous $NaHCO_3$ was added until the pH reached 7-7.2. The resulting slurry was then heated, and a chemical reduction was performed by means of adding sodium formate. During this procedure, gas was released from the slurry and the temperature was further increased to 95° C. Then, the slurry was cooled, decanted or filtered, and washed with fresh demineralised water. Prior to use in the experiments the catalyst was reduced at 180° C. under hydrogen at 10 barg hydrogen for 1 hour.

Example 2a: Reductive Amination of 2-chloro-benzaldehyde with Dimethylamine to Produce 2-Cl-BDMA on a Small Scale A 300 mL autoclave (Parr) was charged with 90 g of 2-chloro-benzaldehyde (industrial grade), 27 g of methanol (industrial grade) and 0.17 g of a catalyst containing, based on dry weight, 3% wt palladium and 7% wt copper on carbon, which had been produced as described in Example 1. The reactor was sealed and the gas phase was flushed three times with nitrogen. Then, an appropriate amount of dimethyl amine was added to the reaction mixture, causing the temperature to increase to about 55° C. in about 5 minutes. Hydrogen was added to a final pressure of 70 barg and the reactor was further heated during about 10 minutes to a reaction temperature of 100° C. and continuously stirred at 500 rpm. The hydrogenation reaction was allowed to proceed for another 2 hours at 100° C. Then, the reactor was cooled down and degassed at room temperature. The catalyst was subsequently filtered off and a sample was taken from the reaction product (i.e. the filtrate) and analysed by GC.

Several experiments were performed using different amounts of dimethyl amine relative to the amount of 2-chloro-benzaldehyde charged. Table 1 below reports the results obtained. The results on the reaction product composition are expressed in weight units relative to the total weight of the reaction product, but disregarding water, methanol and any residual dimethyl amine that might still have been present.

TABLE 1

| | Molar ratio DMA/2-Cl-BZA | | |
|---|---|---|---|
| Composition of the reaction product (wt %) | 1.10 | 1.20 | 1.40 |
| Total o-Cl-BDMA dimers | 0.08 | 0.16 | 0.72 |
| Meso o-Cl-BDMA dimer | 0.03 | 0.07 | 0.34 |
| (+/−)-o-Cl-BDMA dimer | 0.05 | 0.09 | 0.38 |
| 2-chloro-benzyl dimethylamine (2-Cl-BDMA) | 97.80 | 98.30 | 98.00 |
| 2-chloro-benzyl alcohol (2-Cl-BOH) | 0.54 | 0.71 | 0.48 |
| 2-chloro-benzaldehyde (2-Cl-BZA) | 0.16 | 0.06 | 0.01 |
| 4-chloro-benzyl dimethylamine | 0.15 | 0.19 | 0.14 |
| Benzyldimethylamine (BDMA) | 1.01 | 0.37 | 0.36 |

TABLE 1-continued

| | Molar ratio DMA/2-Cl-BZA | | |
|---|---|---|---|
| Composition of the reaction product (wt %) | 1.10 | 1.20 | 1.40 |
| (2-dimethylamino) benzyldimethylamine | 0.19 | 0.15 | 0.26 |
| o-chloro-toluene | 0.00 | 0.00 | 0.00 |
| All toluene chloride isomers together | 0.00 | 0.00 | 0.00 |
| Benzaldehyde (BZA) | ND | ND | ND |

Legend:
ND Not detectable
DMA Dimethyl amine
2-Cl-BZA ortho-chloro-benzyl aldehyde
o-Cl-BDMA ortho-chloro-benzyl dimethyl amine
meso-o-Cl-BDMA dimer (1R,2S)-1,2-bis(2-chlorophenyl)-$N^1,N^1,N^2,N^2$-tetramethyl-ethane-1,2-diamine
(+/−)-o-Cl-BDMA dimer (1R,2R)-1,2-bis(2-chlorophenyl)-$N^1,N^1,N^2,N^2$-tetramethyl-ethane-1,2-diamine together with (1S,2S)-1,2-bis(2-chlorophenyl)-$N^1,N^1,N^2,N^2$-tetramethylethane-1,2-diamine
Total o-Cl-BDMA dimer the meso-o-Cl-BDMA dimer and the (+/−)-o-Cl-BDMA dimer as defined above; (the % wt. of the (+/−)-o-Cl-BDMA dimer was a sum of the (1S,2S) and the (1R,2R) isomer)

The results reported in Table 1 demonstrate that the formation of the meso-o-Cl-BDMA dimer may be suppressed by operating the reductive amination reaction at a molar ratio of DMA/o-Cl-DMA of less than 1.3. The results further illustrate that a lower molar ratio contributes to further reducing the formation of the meso o-Cl-BDMA dimer.

Example 2b: Reductive Amination of 2-chloro-benzaldehyde with Dimethylamine Over a PdAg/AC Catalyst to Produce 2-Cl-BDMA on a Small Scale A 300 mL autoclave (Parr) was charged with 90 g of 2-chloro-benzaldehyde (industrial grade), 30 g of methanol (industrial grade) and 0.27 g of a catalyst containing, based on dry weight, 3% wt palladium and 3% wt silver on carbon. The reactor was sealed and the gas phase was flushed three times with nitrogen. Then, an appropriate amount of dimethyl amine was added to the reaction mixture, causing the temperature to increase to about 55° C. in about 5 minutes. Hydrogen was added to a final pressure of 70 barg and the reactor was further heated during about 10 minutes to a reaction temperature of 100° C. and continuously stirred at 500 rpm. The reaction mixture was evacuated from the closed reaction vessel over a filter leaving the catalyst in the vessel. A sample was taken from the reaction product (i.e. filtrate) and analysed by GC. The reactor was filled again with fresh raw materials and the same batch of catalyst was used for second run with the same conditions. Experiments with 1.2 and 1.4 eq of DMA were performed each with a fresh load of catalyst for three consecutive runs.

Several experiments were performed using different amounts of dimethyl amine relative to the amount of 2-chloro-benzaldehyde charged. The Table below reports the results obtained. The results on the reaction product composition are expressed in weight units relative to the total weight of the reaction product, but disregarding the water that still may be present.

TABLE 1A

| Molar Ratio DMA/2-Cl-BZA: Dimer isomer & content | 1.20 | | | 1.40 | | |
|---|---|---|---|---|---|---|
| | Meso | dl | Total | Meso | dl | Total |
| Run 1 | 0.01% | 0.01% | 0.02% | 0.31% | 0.30% | 0.61% |
| Run 2 | 0.07% | 0.05% | 0.12% | 0.38% | 0.32% | 0.70% |
| Run 3 | 0.11% | 0.08% | 0.19% | 0.33% | 0.29% | 0.62% |

Example 3: Obtainable Final Product Quality

The above operation (according to Example 2a) was performed on a large scale. The reaction product of this large scale operation was filtered to remove the catalyst, and subsequently passed through clean-up steps with the purpose to obtain a final product by the removal, primarily by distillation, of unreacted DMA, unreacted 2-Cl-BZA, water, solvent, benzyl dimethyl amine, and heavies (higher boiling point by-products) comprising the meso-o-Cl-BDMA dimer, the (+/−)-o-CL-BDMA dimer, 2-chloro-benzyl alcohol and (2-dimethylamino) benzyldimethylamine. Table 2 shows the composition of the reaction product and of the final product.

TABLE 2

| Composition | Reaction Product | Final Product |
|---|---|---|
| Total o-Cl-BDMA dimers (ppm wt) | 0.26 | ND |
| Meso o-Cl-BDMA dimer (ppm wt) | 0.12 | ND |
| (+/−)-o-Cl-BDMA dimer (ppm wt) | 0.14 | ND |
| 2-chloro-benzyl dimethylamine (% wt) | 71.80 | 99.79 |
| 2-chloro-benzyl alcohol (2-Cl-BOH) | 0.54 | 0.012 |
| 2-chloro-benzaldehyde (2-Cl-BZA) | 0.012 | 0.029 |
| 4-chloro-benzyl dimethylamine | 0.135 | 0.102 |
| Benzyldimethylamine (BDMA) | 0.274 | 0.011 |
| (2-dimethylamino) benzyldimethylamine | 0.122 | 0.019 |
| o-chloro-toluene (% wt) | 0.006 | 0.005 |
| All toluene chloride isomers together (% wt) | 0.020 | 0.007 |
| Benzaldehyde (BZA) | <0.001 | <0.001 |

Example 4: Catalyst Life Time Test

Figure 2:
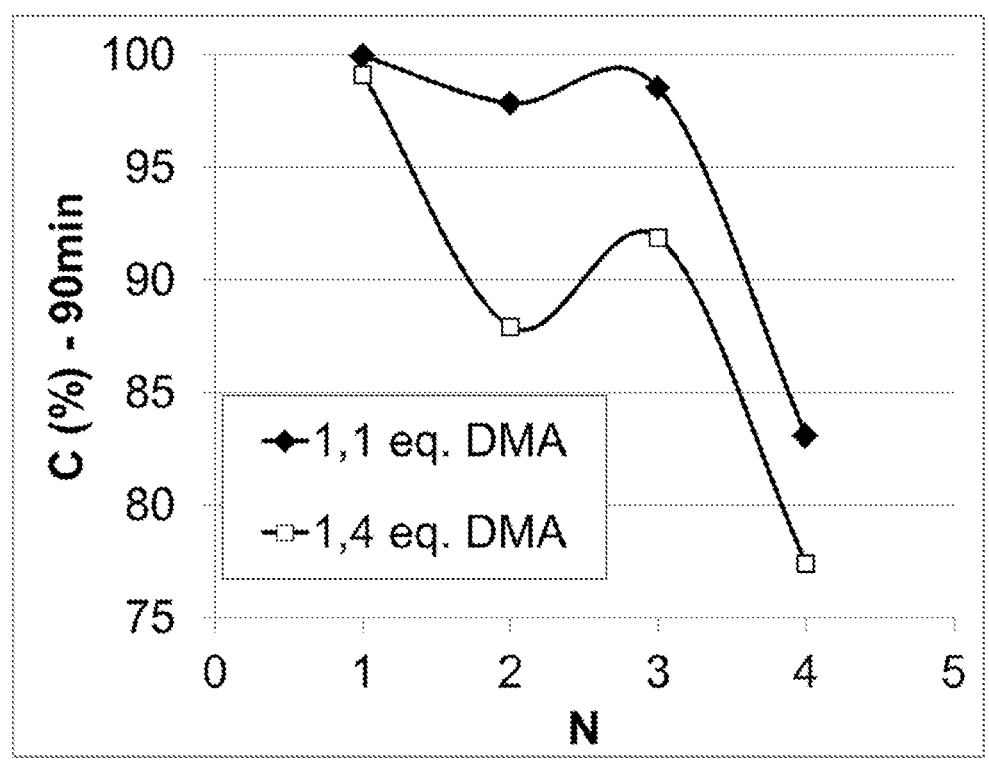
FIG. 2 contains a graph of C (%)—90 min vs N, showing the evolution of the percent of conversion of the starting substrate 2-Cl-BZA obtained in each batch run after 90 minutes of reaction time.

Two short life time tests were performed with each time a new lot of catalyst produced as in Example 1. The catalyst was each time used in four consecutive reaction batches performed as in Example 2. The first life time test was performed with an amount of DMA of 1.4 molar equivalents to the 2-Cl-BZA substrate, and the second test used a molar ratio of only 1.1. FIG. 1 contains a graph of mD (wt %) vs N, showing the evolution of the amount of the meso-o-Cl-BDMA dimer which was found in the reaction mixture from these tests, expressed in wt % relative to the amount of 2-Cl-BDMA product retrieved in the same sample, in the reaction products from the consecutive batch runs. FIG. 2 contains a graph of C (%)—90 min vs N, showing the evolution of the percent of conversion of the starting substrate 2-Cl-BZA obtained in each batch run after 90 minutes of reaction time.

These experiments illustrate that the lower molar ratio of DMA leads to a lower dimer formation, and illustrate further that the dimer formation not only remains low but also remains more stable over time and during subsequent runs.

FIG. 2 shows that operating at a lower molar ratio of DMA/2-Cl-BZA also reduces the deactivation rate of the catalyst.

The effects shown in the graphs of FIGS. 1 and 2 was confirmed on a commercial scale. While a campaign operated with a molar equivalent of 1.4 had to be stopped after 4 batch runs because of operational problems, later campaigns operated with a molar DMA equivalent presence of only 1.1 were able to continue for at least 13 consecutive runs without incurring operational problems or before observing a catalyst deactivation which would necessitate a replacement of the catalyst charge. The dimer concentrations in the consecutive reaction products showed a trend in conformity with the above short life time test.

It will be appreciated by those skilled in the art that the invention can be performed within a wide range of parameters within what is claimed, without departing from the scope of the invention, as defined by the claims.

The invention claimed is:

1. A process for performing a reductive amination of a halo-benzaldehyde in the presence of hydrogen, a nitrogen-containing compound, and a heterogeneous catalyst comprising ruthenium, rhodium, iridium, palladium, or platinum, on a carbon support, wherein the presence of the nitrogen-containing compound, expressed in a molar ratio relative to the halo-benzaldehyde, at least during a period of the reaction as long as the conversion of the halo-benzaldehyde has not yet reached 80%, is maintained below a level of 1.3; wherein the nitrogen containing compound has the formula R1-NH—R2, and R1 and R2 are independently selected from a $C_1$ to $C_{10}$ alkyl group and an aryl group, optionally substituted with an alkyl group.

2. The process according to claim 1 wherein the molar ratio of the nitrogen-containing compound, relative to the halo-benzaldehyde, is maintained at least during the period as defined in claim 1 of the reaction at a level of at least 0.10.

3. The process according to claim 1 wherein the molar ratio of the nitrogen-containing compound, relative to the halo-benzaldehyde, is maintained at a level of less than 1.25.

4. The process according to claim 1 wherein the nitrogen-containing compound is, at least during the period of the reaction as defined in claim 1, added gradually.

5. The process according to claim 1 wherein the reductive amination reaction is performed until at least 50% of the halo-benzaldehyde present in the reaction medium is converted.

6. The process according to claim 1 wherein the halogen atom on the halo-benzaldehyde is selected from a chloride, a bromide, an iodide or a fluoride.

7. The process according to claim 1 wherein the carbon support comprises carbon or an activated carbon.

8. The process according to claim 1 wherein the heterogeneous catalyst comprises palladium, platinum, rhodium, iridium, or ruthenium, together with at least one second metal selected from the list consisting of silver, nickel, cobalt, iron, tin, lead, bismuth, gold, and copper.

9. The process according to claim 1 wherein the catalyst comprises palladium, platinum, rhodium, iridium, or ruthenium, and in absence of a catalytic amount of any second metal selected from the list consisting of silver, nickel, cobalt, tin, bismuth, copper, gold, and combinations thereof, whereby the heterogeneous catalyst has been heat-treated prior to the reductive amination at a temperature in the range of 100° C. to 600° C. for a period of at least two hours.

10. The process of claim 1, wherein the catalyst comprises Pd and Ag.

11. The process according to claim 1, comprising the production of ortho-chloro benzyl dimethyl amine, 2-Cl-BDMA, and optionally, further comprising subjecting the 2-Cl-BDMA to a Grignard reaction.

12. The process of claim 7, wherein the support carbon which has been activated by a treatment with an acid.

* * * * *